(12) United States Patent
Burgoon, Jr. et al.

(10) Patent No.: US 7,919,618 B2
(45) Date of Patent: Apr. 5, 2011

(54) SYNTHESIS OF PIPERAZINES, PIPERIDINES AND RELATED COMPOUNDS

(75) Inventors: Hugh Alfred Burgoon, Jr., Hamilton, NJ (US); Ramanaiah C. Kanamarlapudi, Bridgewater, NJ (US); Wenxue Wu, Princeton Junction, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 898 days.

(21) Appl. No.: 11/832,738

(22) Filed: Aug. 2, 2007

(65) Prior Publication Data
US 2008/0177070 A1    Jul. 24, 2008

Related U.S. Application Data

(60) Provisional application No. 60/835,679, filed on Aug. 4, 2006.

(51) Int. Cl.
*C07D 401/04* (2006.01)
*C07D 401/14* (2006.01)
*C07D 403/04* (2006.01)
*C07D 403/14* (2006.01)

(52) U.S. Cl. ........ 544/330; 544/331; 544/332; 544/334; 540/598

(58) Field of Classification Search .................. 544/330, 544/331, 332, 334; 540/598; 514/598
See application file for complete search history.

(56) References Cited

U.S. PATENT DOCUMENTS

2006/0258672 A1  11/2006  Fink
2006/0258691 A1  11/2006  Barbosa
2008/0076788 A1   3/2008  Barbosa

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
International Search Report issued in connection with corresponding international application PCT/US2007/075026, dated Feb. 12, 2008.
Birch et al., *J. Med. Chem.*, 42(17), 3342-3355 (1999).
Zhang et al., *Tetrahedron Letters*, 41(5), 595-598 (2000).

* cited by examiner

*Primary Examiner* — Venkataraman Balasubramanian
(74) *Attorney, Agent, or Firm* — Max Bachrach

(57) ABSTRACT

Novel methods of synthesizing piperazines, piperidines and related compounds are disclosed, as are compounds useful for their preparation.

29 Claims, No Drawings

SYNTHESIS OF PIPERAZINES, PIPERIDINES AND RELATED COMPOUNDS

This application claims priority to U.S. provisional patent application no. 60/835,679, filed Aug. 4, 2006, the entirety of which is incorporated herein by reference.

1. FIELD OF THE INVENTION

This invention relates to novel methods of synthesizing piperazines, piperidines and related compounds, and to intermediates useful for their preparation.

2. BACKGROUND OF THE INVENTION

It is believed that piperazines, piperidines and related compounds may be useful in the treatment of a variety of diseases, including diseases of the central nervous system. Consequently, a need exists for methods of preparing such compounds that are cost effective, efficient and provide good yields.

3. SUMMARY OF THE INVENTION

This invention encompasses novel methods of preparing piperazines, piperidines and related compounds. Particular embodiments of the invention allow the efficient, large scale synthesis of such compounds.

One embodiment of the invention encompasses a method of preparing a compound of formula I:

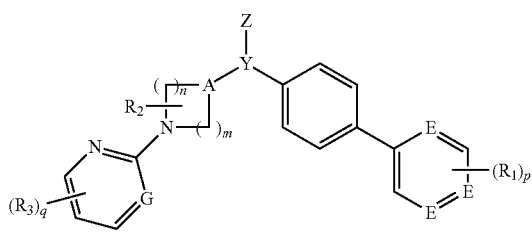

or a salt or solvate thereof, which comprises contacting a compound of formula IV with a compound of formula V:

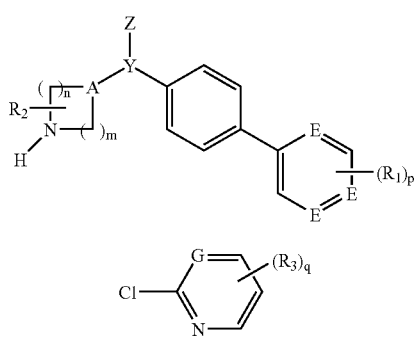

under conditions sufficient for the formation of the compound of formula I, wherein the various substituents are defined below.

Another embodiment encompasses a method of preparing a compound of formula IV, which comprises contacting a compound of formula II and a compound of formula III

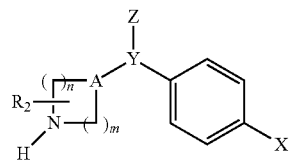

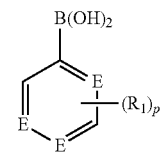

with a transition metal catalyst under conditions sufficient for the formation of the compound of formula IV.

This invention also encompasses novel intermediates useful in methods disclosed herein, such as (3'-chloro-biphenyl-4-yl)-piperidine-4-yl-methanone, and salts and solvate thereof.

4. DETAILED DESCRIPTION OF THE INVENTION

This invention encompasses methods of preparing compounds of formula I:

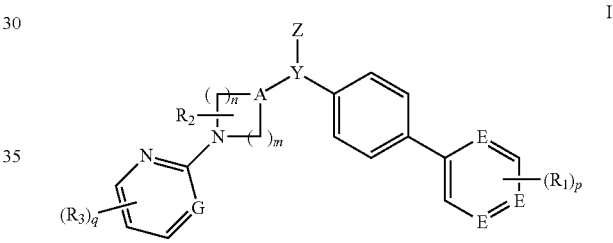

and salts and solvate thereof, wherein: Y—Z is C(O), O, CHOH or $CH_2$; A is N or CH; G is CH or N; each E is independently N or CH; each $R_1$ is independently fluorine, chlorine or optionally substituted alkyl, aryl, or aralkyl; $R_2$ is H or =O; each $R_3$ is independently H, fluorine, chlorine or optionally substituted alkyl, aryl, aralkyl, heterocycle, or heterocycloalkyl; m is 1, 2 or 3; n is 1 or 2; p is 1 or 2; and q is 1-3.

Specific compounds of formula I are inhibitors of the $Na^+$-dependent proline transporter, and may be used for the improvement of cognitive performance and for the treatment, prevention and/or management of diseases and disorders such as Alzheimer's disease, autism, cognitive disorders, dementia, learning disorders, and short- and long-term memory loss. See U.S. patent application Ser. Nos. 11/433,057 and 11/433,626, both filed May 12, 2006.

One embodiment of the invention encompasses a method of preparing a compound of formula I:

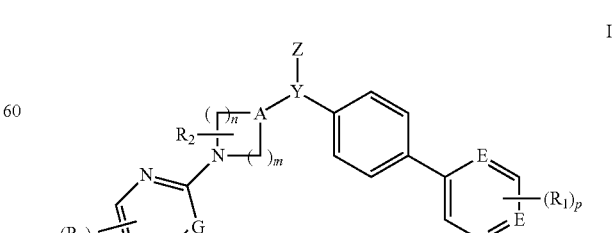

or a salt or solvate thereof, which comprises contacting a compound of formula IV with a compound of formula V:

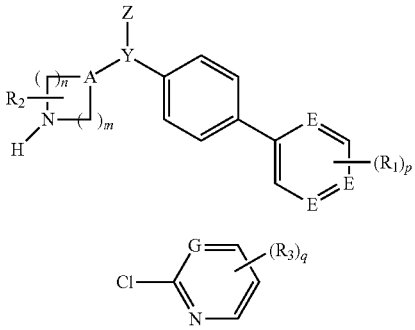

IV

V under conditions sufficient for the formation of the compound of formula I.

The compound of formula IV can be prepared by contacting a compound of formula II and a compound of formula III

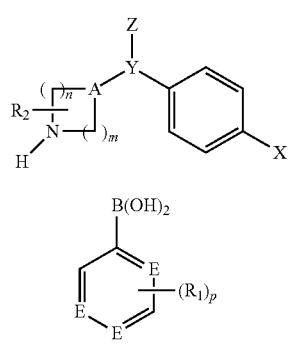

II

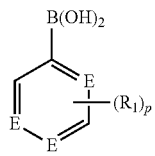

III with a transition metal catalyst under conditions sufficient for the formation of the compound of formula IV, wherein X is Br or I.

In a particular method, the catalyst is a palladium catalyst (e.g., comprises encapsulated or polymer-bound palladium), such as bis(triphenylphosphine)-palladium(II) dichloride.

In another, the catalyst is present in an amount of from about 0.1 to about 7.5 mol percent or about 0.5 to about 5.0 mol percent. In a specific method, the catalyst is present in an amount of about 0.5 mol percent.

In a particular embodiment, Y—Z is C(O). In another, A is CH. In another, each E is CH. In another, p is 1 and $R_1$ is chlorine. In another, n and m are both 2.

In another, the compounds of formulae II and III are in solution (e.g., a solution comprising an alcohol).

In another, the compound of formula IV is extracted using an aqueous acidic solution (e.g., a solution comprising lactic acid). In another, the compound of formula IV is isolated as a salt.

A particular method encompassed by the invention is a method of preparing (3'-chloro-biphenyl-4-yl)-(1-pyrimidin-2-yl-piperidin-4-yl)-methanone, or a salt or solvate thereof, which comprises contacting (3'-chloro-biphenyl-4-yl)-piperidine-4-yl-methanone with 2-chloropyrimidine under conditions sufficient for the formation of (3'-chloro-biphenyl-4-yl)-(1-pyrimidin-2-yl-piperidin-4-yl)-methanone. In one embodiment, wherein the conditions sufficient for the formation of (3'-chloro-biphenyl-4-yl)-(1-pyrimidin-2-yl-piperidin-4-yl)-methanone are basic conditions.

Another particular method is a method of preparing (3'-chloro-biphenyl-4-yl)-piperidine-4-yl-methanone or a salt thereof, which comprises contacting 3-chlorophenyl boronic acid and (4-bromophenyl)(piperidine-4-yl)methanone with a transition metal catalyst under conditions sufficient for the formation of 3'-chloro-biphenyl-4-yl)-piperidine-4-yl-methanone. In one embodiment, the catalyst is a palladium catalyst (e.g., a catalyst comprising encapsulated or polymer-bound palladium), such as bis(triphenylphosphine)-palladium(II) dichloride.

This invention also encompasses novel intermediates useful in the processes disclosed herein, such as (3'-chloro-biphenyl-4-yl)-piperidine-4-yl-methanone, and salts and solvate thereof.

4.1. Definitions

Unless otherwise indicated, the term "alkyl" means a saturated straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Examples of cycloalkyl groups include, but are not limited to, cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes "alkenyl" and "alkynyl" moieties.

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means a an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" means an aryl moiety bound to an alkyl moiety.

Unless otherwise indicated, the terms "halogen" and "halo" refer to fluorine and chlorine.

Unless otherwise indicated, the term "heteroalkyl" refers to an alkyl moiety in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" means a heteroaryl moiety bound to an alkyl moiety.

Unless otherwise indicated, the term "heterocycle" refers to an aromatic, partially aromatic or non-aromatic, monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydro furanyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocycloalkyl" refers to a non-aromatic heterocycle.

Unless otherwise indicated, the term "heterocycloalkylalkyl" refers to a heterocycloalkyl moiety bound to an alkyl moiety.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol (e.g., hydroxyl, alkyl-OH), aldehylde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)Nhalkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, the term "include" has the same meaning as "include, but are not limited to." Similarly, the term "includes" has the same meaning as "includes, but is not limited to."

Unless otherwise indicated, an adjective before a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that if there is a discrepancy between a depicted structure and a name given that structure, the structure should be accorded more weight. In addition, if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences.

4.2. Methods of Synthesis

Arylpiperazines, arylpiperidines, and related compounds are prepared using a Suzuki reaction followed by an aromatic nucleophilic substitution reaction:

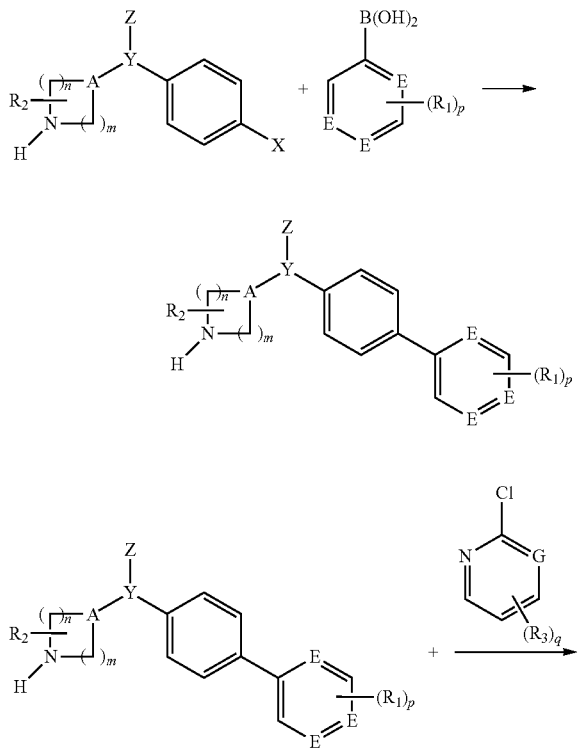

Scheme 1

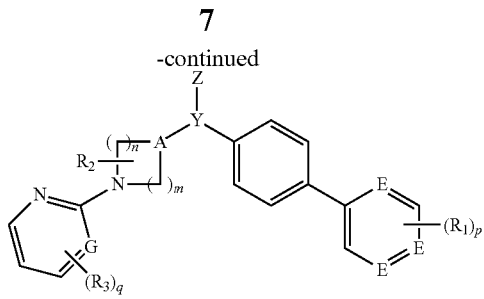

wherein X, Y, Z, A, E, $R_1$-$R_3$, n, m, p and q are defined herein. Of course, potentially reactive moieties encompassed by the definitions of $R_1R_3$ may be protected using methods known in the art. Moreover, the final product may undergo further reactions known in the art to afford other compounds encompassed by formula I (e.g., Y—Z may be C(O), which may be reduced to afford CHOH and $CH_2$).

4.2.1. Suzuki Reaction

Depending on the reactants and reaction conditions, Suzuki reactions can afford various undesired side products. For example, when used to prepare (3'-chloro-biphenyl-4-yl)-piperidin-4-yl-methanone A from (4-bromo-phenyl)-piperidin-4-yl-methanone and 3-chlorophenyl boronic acid, the reaction can form dehalogenated starting material B, dehalogenated product C, double Suzuki product D and homocoupling product E, as shown below in Scheme 2:

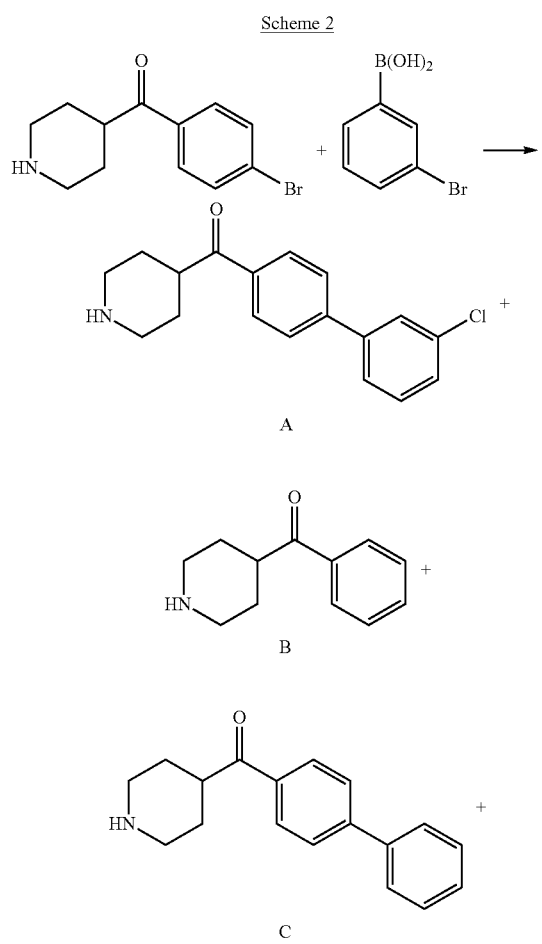

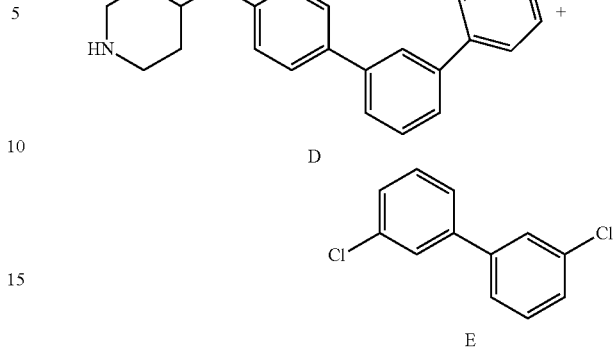

This is particularly problematic, since side products B, C and D will react in the second step of the process, providing compounds that are difficult to separate from the desired final product. Advantageously, methods of this invention reduce the formation of such products.

In general, the Suzuki reaction utilizes a palladium catalyst (e.g., Pd/C, $PdCl_2(PPh_3)_2$, Pd-EnCat™, FibreCat®, $Pd(PPh_3)_4$, $Pd(OAc)_2$) which is contacted with the starting materials in a suitable solvent at a suitable temperature for a suitable amount of time. But it was discovered that the choice of catalyst and conditions will affect the generation of side products. Moreover, their formation can depend on the scale of the reaction. For example, on a small scale (e.g., 1-2 grams starting material), the use of Pd/C as a catalyst yielded a minimum of side products, which could be separated by ISCO column chromatography (Teledyne Isco, Inc., Lincoln, Nebr.). But when used in large scale (e.g., 10 grams of starting material) reactions, dehalogenated staring material and products were increased to about 20-30 percent, and were difficult to remove by crystallization or column chromatography. In contrast, the encapsulated palladium catalyst Pd-EnCat™ (described in PCT/GB 02/03135 and available from Sigma-Aldrich, Milwaukee, Wis.) and the anchored palladium catalyst FibreCat® (Johnson Matthey, Houston, Tex.) provide the expected product in high yield and minimal (<3%) dehalogenated products. The much less expensive bis(triphenylphosphine)palladium(II) dichloride ($PdCl_2(PPh_3)_2$) gives similar results, although its use results in large amounts of residual palladium in the final product. Advantageously, the present invention can provide a final product with acceptable palladium levels.

The reaction may be conducted in any suitable solvent or solvent system, including ethanol, methanol, acetonitrile, isopropanol, water and mixtures thereof. The reaction is preferably done in a mixture of alcohol solvent with water, more preferably isopropanol/water solvent system (e.g., in proportions of about 12:3).

Although any amount of catalyst suitable to take the reaction to completion may be used, typical amounts range from about 0.1 to about 7.5 mol percent, preferably from about 0.5 to about 5.0 mol percent, relative to the amount of starting material. A specific amount is about 0.5 mol percent.

The temperature at which the reaction is run can vary depending on the catalyst, its amount, and the solvent system. For example, the reaction may be run at about 50° C., but may require more catalyst (e.g., about 5 mol percent) and may take more time (e.g., about 14 hours). A reaction run at about 80° C. requires less catalyst, and may take as little as 2-3 hours.

How the desired product is obtained upon completion of the reaction can depend on the catalyst used. For example, the use of PdCl$_2$(PPh$_3$)$_2$ requires the removal of residual palladium (e.g., to levels of less than about 50 ppm). This can be achieved by isolating the product by acidic extraction or salt formation. Acidic extraction is preferably done with lactic acid. Salt precipitation can be effected using H$_3$PO$_4$ or HCl. A preferred salt is HCl (e.g., isolated from ethyl acetate:ethanol about 95:5), which can afford the Suzuki reaction product with high purity.

4.2.2. Nucleophilic Substitution

The nucleophilic substitution step shown above in Scheme 2 is a base catalyzed reaction, which may be run in a variety of different solvents, including alcohols, amides, esters, ethers, nitriles, and chlorinated solvents. Examples of suitable bases include potassium carbonate, cesium carbonate and tertiary organic amines.

Preferably, the final product of formula I is purified by crystallization.

5. EXAMPLES

The compound (3'-chloro-biphenyl-4-yl)-(1-pyrimidin-2-yl-piperidin-4-yl)-methanone was prepared according to Scheme 3:

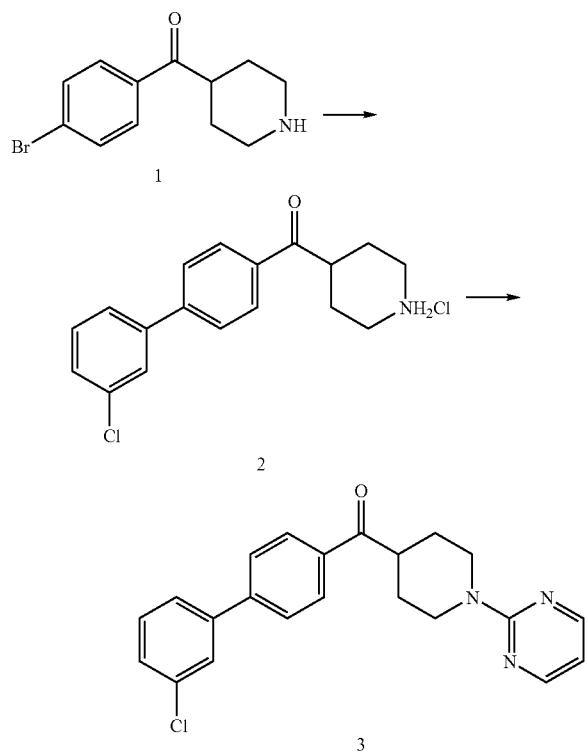

5.1. Preparation of (3'-Chloro-biphenyl-4-yl)-piperidine-4-yl-methanone hydrochloride (2)

(3'-Chloro-biphenyl-4-yl)-piperidine-4-yl-methanone hydrochloride (2) was prepared by three different methods, identified below as A, B and C.

Method A:

3-Chlorophenyl boronic acid (Alfa Aesar, purity 97%)(40.7 g, 261.19 mmol, 1.4 eq) was dissolved in isopropanol (Aldrich, ACS reagent grade) (800 ml) under nitrogen atmosphere. This was added to a solution of aqueous potassium carbonate (77 g in 150 ml water), bis(triphenylphosphine)palladium(II) dichloride (PdCl$_2$(PPh$_3$)$_2$) (0.65 g, 0.93 mmol, 0.5 mol. eq.) and (4-bromophenyl)(piperidine-4-yl)methanone (1) (50 g, 187 mmol, 1 eq) were stirred at 80° C. for three hours and deemed complete by LC/MS. After the reaction mixture cooled down to 50° C., it was filtered through celite pad, washed with methanol (1 liter). The filtrate was diluted with water (200 ml), then the organic solvent removed under reduced pressure. The resulting crude product was dissolved in ethyl acetate (800 ml) and washed with 1N sodium hydroxide (2×40 ml) and water (1×40 ml).

The organic layer was stirred with aqueous lactic acid (64 g of 85% lactic acid in 600 ml of water) at 50° C. for 20 minutes. After the organic layer was separated (solution assay indicated 8% of product present in the organic layer, which can be captured by additional lactic acid extraction), the aqueous layer was washed with ethyl acetate (2×100 ml). The aqueous layer was separated, basified to pH=11 with 25% NaOH (70 ml), and then extracted with ethyl acetate (2×200 ml), dried over sodium sulfate, filtered and concentrated under reduced pressure to obtained biaryl product 46.23 g (83%) as a syrup. HPLC indicated 99.4% product and 0.57% of debrominated staring material.

The above product was dissolved in mixture of ethyl acetate (900 ml) and ethanol (45 ml) and heated at 50° C. 6M aq. HCl (40 ml) was added dropwise over a period of ten minutes. After 20 minutes, the reaction mixture was cooled to room temperature, and stirring was continued for an additional hour. The resulting white solid was filtered and dried under vacuum at 50° C. for five hours to afford 49.8 grams of the biaryl HCl salt 2 (80%). HPLC indicated pure product.

$^1$H NMR (DMSO-d$_6$) δ: 1.92 (m, 4H), 2.52 (m, 2H), 3.12 (m, 2H), 3.82 (m, 1H), 7.51 (m, 2H), 7.75 (m, 1H), 7.82 (br s, 1H), 7.92 (bs d, 2H), 8.12 (brd, 2H), 9.0 (br s, 2H). MH$^+$=300, 302 (about 3:1). Palladium: 15 ppm.

Method B

A round bottom flask was charged with (4-bromophenyl)(piperidine-4-yl)methanone (20.0 g, 74.6 mmol), 3-chlorophenyl boronic acid (17.4 g, 111 mmol, 1.5 eq), and palladium encapsulated catalyst (Aldrich, Pd EnCat-TPP®, catalyst species PdCl$_2$(PPh$_3$)$_2$) (5.2 g, 0.187 mmol, 0.05 eq). These solids were suspended in isopropanol (570 ml) and allowed to stir for five minutes. To the mixture was added potassium carbonate (30.8 g, 224 mmol, 3 eq) dissolved in H$_2$O (30 ml). The reaction mixture was heated to 80° C. for 16 hours and deemed complete by LC/MS. The suspension was filtered through a small bed of Celite® and the filtrate was concentrated to dryness. The resulting solids were dissolved in isopropyl acetate (400 ml) and washed with water (3×75 ml). The organic layer was then cooled to 0° C. (ice/water bath) and to this stirring solution was added slowly 6 N HCl until solids crystallized. The solids were filtered and dried in a vacuum oven for 16 hours at 50° C. to afford 16.9 g of compound 2 (68% yield) in >98% HPLC purity. MH$^+$=300, 302 (about 3:1). Palladium: 3 ppm.

Method C

A round bottom flask was charged with (4-bromophenyl)(piperidine-4-yl)methanone (4.00 g, 14.9 mmol), 3-chlorophenyl boronic acid (3.26 g, 20.9 mmol, 1.4 eq), and Fibrecat 1029® (0.70 g, 0.448 mmol, 0.03 eq, Johnson Matthey). These solids were suspended in isopropanol (68 ml) and allowed to stir for five minutes. To this stirring solution was added potassium carbonate (6.18 g, 44.8 mmol, 3 eq.) dissolved in H$_2$O (12 ml). The resulting solution was heated to 80° C. for 16 hours, at which time the reaction was deemed complete by LC/MS. The reaction mixture was filtered through a small bed of Celite® and the filtrate was concentrated to dryness. The resulting solids were dissolved in isopropyl acetate (100 ml) and washed with water (3×50 ml). The organics were cooled to 0° C., and to this stirring mixture was added slowly 6N HCl until solids crashed out of solution. The solids were filtered and dried for 16 hours at 50° C. in a vacuum oven to afford 2.89 g of compound 2 (72%) in >98% HPLC purity. MH$^+$=300, 302 (about 3:1). Palladium: 4 ppm

5.2. Preparation of (3'-Chloro-biphenyl-4-yl)-(1-pyrimidin-2-yl-piperidine-4-yl)-methanone (3)

A mixture of (3'-chloro-biphenyl-4-yl)-piperidine-4-yl-methanone hydrochloride salt (40 g, 119.4 mmol), 2-chloropyrimidine (19 g, 167.16 mmol, 1.4 eq), potassium carbonate (325 mesh, Aldrich) (49.4 g, 358.2 mmol, 3 eq) and acetonitrile (560 ml) were stirred at 60° C. for 14 hours and deemed complete by LC/MS. The reaction mixture was concentrated, and the residue was dissolved in ethyl acetate (800 ml) and water (200 ml). The aqueous layer was separated and extracted with ethyl acetate (1×200 ml). The organic layers were combined and washed with brine (1×50 ml), dried and concentrated.

Crystallization

The above product was taken into ethanol (700 ml) and stirred with a mechanical stirrer at 70° C. After 30 minutes, the solid was completely dissolved. At that time, the reaction temperature was decreased to 45° C. and stirred for 4 hours (heterogeneous mixture). The reaction mixture was then stirred at room temperature for 3 hours. The resulting white solid was filtered washed with ethanol (50 ml), dried at 50° C. for 5 hours. This gave product 3 in 84.4% yield (33.9 g) as a white solid. 100% pure by HPLC.

$^1$H NMR (CDCl$_3$) δ: 1.75 (m, 2H), 1.92 (m, 2H), 3.05 (m, 2H), 3.50 (m, 1H), 4.75 (m, 2H), 6.42 (t, 1H), 7.32 (m, 2H), 7.4 (m, 1H), 7.51 (s, 1H), 7.62 (d, 2H), 7.95 (d, 2H), 8.22 (d, 2H). $^{13}$CNMR (CDCl$_3$): 28.72, 43.79, 44.34, 110.2, 125.82, 127.78, 127.81, 128.63, 129.39, 130.62, 135.29, 135.49, 142.03, 144.62, 158.13, 161.93, 202.09. MH$^+$=378, 380 (about 3:1 ratio). Palladium: 2 ppm.

5.3. Large-Scale Procedure for the Preparation of (3'-Chloro-biphenyl-4-yl)-piperidine-4-yl-methanone hydrochloride (2)

(4-Bromophenyl)(piperidine-4-yl)methanone (1, 22 kg, 82.1 mol), 3-chlorophenyl boronic acid (14.1 kg, 1.1 equiv), aqueous potassium carbonate (35 kg, 3 equiv, in 66 L water), (Ph$_3$)$_2$PdCl$_2$ (0.28 kg, 0.5% mol) were mixed in isopropanol (IPA, 264 L) in a 300-gallon reactor. The cloudy yellow mixture was heated to 75-85° C. until the reaction is complete. The batch was cooled to 45-55° C. and the aqueous layer was separated. The organic layer was filtered through a diatomaceous earth pad and vacuum concentrated to about 100 L to give a cloudy yellow solution, which was diluted with isopropyl acetate (IPAc, 176 L). The resulting mixture was washed with 1 N NaOH (18 L) and separated and the aqueous phase was extracted with IPAc (44 L). The combined organic layers were washed with 1 N NaOH (18 L), and then water (18 L) and transferred to a clean 300-gallon reactor followed by water (176 L) and 85% lactic acid (30 kg, 3.3 equiv). The batch was heated to 50-60° C. and stirred at this temperature for 2 h before separation. The aqueous phase containing the batch was transferred to a clean 100-gallon reactor followed by the addition of 25% (w/w) NaOH (about 44 L) while maintaining the temperature at 30-40° C. until the pH was between 10.5-11. The aqueous phase was then extracted with IPAc (2×88 L) and the resulting combined organic layers were filtered through an in-line filter into a clean 300-gallon reactor. IPAc (147 L) and IPA (20 L) were charged to the batch before being heated to 45-55° C. Aqueous 6 N hydrochloric acid (20 L) was then added via the drop tank while maintaining the batch temperature at ≦55° C. After 30 min, the heating was discontinued and the resulting slurry was cooled to 15-25° C. The batch was filtered and the filter cake washed with IPAc (2×31 L) and dried at 40-50° C. under vacuum to afford HCl salt Compound 2 (23.4 kg, 84% yield, >99% purity) as an off-white crystalline solid.

5.4. Large-Scale Preparation of (3'-Chloro-biphenyl-4-yl)-(1-pyrimidin-2-yl-piperidine-4-yl)-methanone (3)

(3'-Chloro-biphenyl-4-yl)-piperidine-4-yl-methanone hydrochloride (2, 23.4 kg, 69.6 mol), 2-chloropyrimidine (8.9 kg, 1.3 equiv), and 325-mesh potassium carbonate (25 kg, 3 equiv) were mixed in acetonitrile (211 L) in a 100-gallon reactor. The batch was heated with agitation at 55-65° C. for 16 h. The batch was then cooled to 20-30° C., followed by the addition of water (70 L) and further stirred for 15 min. The batch was transferred to a 300-gallon reactor and rinsed with water (360 L) to afford a thick white suspension. After stirring for 2 h, the batch was filtered and washed with water (2×70 L) and dried to constant weight at 45-55° C. to afford crude compound 3 (23.5 kg, 89.5% yield, >99% purity) as a white crystalline solid.

5.5. Large-Scale Recrystallization of (3'-Chloro-biphenyl-4-yl)-(1-pyrimidin-2-yl-piperidine-4-yl)-methanone (3)

Recrystallization of (3'-chloro-biphenyl-4-yl)-(1-pyrimidin-2-yl-piperidine-4-yl)-methanone (3) can be carried out as follows. (3'-Chloro-biphenyl-4-yl)-(1-pyrimidin-2-yl-piperidine-4-yl)-methanone (3, 19.8 kg) was dissolved in ethanol (307 L) in a 100-gallon reactor at 70-80° C. The batch was then clarified through a preheated inline filter to a new, clean preheated 100-gallon reactor, followed by further cooling to 15-25° C. over a 4-h period and aged for an additional 3 h. The resulting solids were isolated by filtration and the resulting cake was washed with ethanol (2×40 L) and dried at 45-55° C. under vacuum for 24 hours to afford Compound 3 (19.8 kg, 84% yield, >99% purity) as a white crystalline solid.

All references (e.g., patents and patent applications) cited above are incorporated herein by reference in their entireties.

What is claimed is:
1. A method of preparing a compound of formula I:

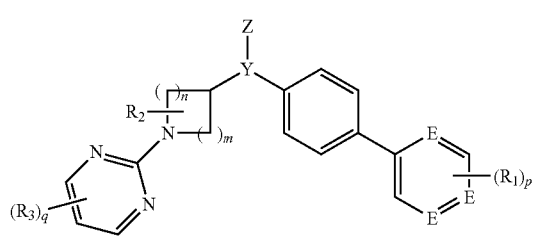

or a salt thereof, which comprises contacting a compound of formula IV with a compound of formula V:

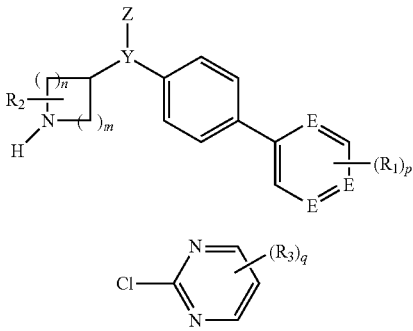

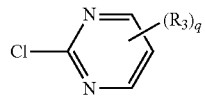

under conditions sufficient for the formation of the compound of formula I, wherein:
Y-Z is C(O), O, CHOH or $CH_2$;
each E is independently N or CH;
each $R_1$ is independently fluorine, chlorine or optionally substituted alkyl, aryl, or aralkyl;
$R_2$ is H or =O;
each $R_3$ is independently hydrogen, alkyl, aryl, aralkyl, heterocycle, or heterocycloalkyl;
m is 1, 2 or 3;
n is 1 or 2;
p is 1 or 2; and
q is 1-3.

2. The method of claim 1, wherein the conditions sufficient for the formation of the compound of formula I are basic conditions.

3. The method of claim 1, wherein the compound of formula IV is prepared by contacting a compound of formula II and a compound of formula III

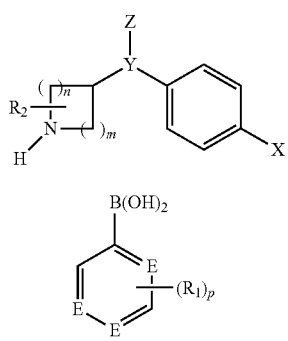

with a transition metal catalyst under conditions sufficient for the formation of the compound of formula IV, wherein X is Br or I.

4. The method of claim 3, wherein the catalyst is a palladium catalyst.

5. The method of claim 4, wherein the catalyst comprises encapsulated or polymer-bound palladium.

6. The method of claim 4, wherein the catalyst is bis(triphenylphosphine)palladium(II) dichloride.

7. The method of claim 3, wherein the catalyst is present in an amount of from about 0.1 to about 7.5 mol percent.

8. The method of claim 1, wherein Y—Z is C(O).

9. The method of claim 1, wherein each E is CH.

10. The method of claim 1, wherein p is 1 and $R_1$ is chlorine.

11. The method of claim 1, wherein n and m are both 2.

12. The method of claim 3, wherein Y—Z is C(O).

13. The method of claim 3, wherein each E is CH.

14. The method of claim 3, wherein p is 1 and $R_1$ is chlorine.

15. The method of claim 3, wherein n and m are both 2.

16. The method of claim 3, wherein the compounds of formulae II and III are in solution.

17. The method of claim 16, wherein the solution comprises an alcohol.

18. The method of claim 3, wherein the compound of formula IV is extracted using an aqueous acidic solution.

19. The method of claim 18, wherein the solution comprises lactic acid.

20. The method of claim 3, wherein the compound of formula IV is isolated as a salt.

21. The method of claim 20, wherein the salt is a hydrochloride or phosphate salt.

22. A method of preparing (3'-chloro-biphenyl-4-yl)-(1-pyrimidin-2-yl-piperidin-4-yl)-methanone, or a salt thereof, which comprises contacting (3'-chloro-biphenyl-4-yl)-piperidine-4-yl-methanone with 2-chloropyrimidine under conditions sufficient for the formation of (3'-chloro-biphenyl-4-yl)-(1-pyrimidin-2-yl-piperidin-4-yl)-methanone.

23. The method of claim 22, wherein the conditions sufficient for the formation of (3'-chloro-biphenyl-4-yl)-(1-pyrimidin-2-yl-piperidin-4-yl)-methanone are basic conditions.

24. A method of preparing (3'-chloro-biphenyl-4-yl)-piperidine-4-yl-methanone or a salt thereof, which comprises contacting 3-chlorophenyl boronic acid and (4-bromophenyl)(piperidine-4-yl)methanone with a transition metal catalyst under conditions sufficient for the formation of 3'-chloro-biphenyl-4-yl)-piperidine-4-yl-methanone.

25. The method of claim 24, wherein the catalyst is a palladium catalyst.

26. The method of claim 25, wherein the catalyst comprises encapsulated or polymer-bound palladium.

27. The method of claim 25, wherein the catalyst is bis(triphenylphosphine)palladium(II) dichloride.

28. The method of claim 25, wherein the catalyst is present in an amount of from about 0.1 to about 7.5 mol percent.

29. The method of claim 28, wherein the catalyst is present in an amount of about 0.5 mol percent.

* * * * *